(12) United States Patent
Zhang et al.

(10) Patent No.: US 11,523,795 B2
(45) Date of Patent: Dec. 13, 2022

(54) HEART SOUND MONITORING DEVICE AND METHOD FOR ACQUIRING HEART SOUND SIGNAL

(71) Applicants: BEIJING BOE DISPLAY TECHNOLOGY CO., LTD., Beijing (CN); BOE TECHNOLOGY GROUP CO., LTD., Beijing (CN)

(72) Inventors: Xuru Zhang, Beijing (CN); Qian Wang, Beijing (CN); Duo Zhang, Beijing (CN); Yinghao Zhang, Beijing (CN); Weimeng Zhang, Beijing (CN); Feng Jiang, Beijing (CN); Yanjie Zhang, Beijing (CN); Dongxue Sun, Beijing (CN); Yongquan Lu, Beijing (CN)

(73) Assignees: BEIJING BOE DISPLAY TECHNOLOGY CO., LTD., Beijing (CN); Beijing BOE Technology Development Co., Ltd., Beijing (CN)

( * ) Notice: Subject to any disclaimer, the term of this patent is extended or adjusted under 35 U.S.C. 154(b) by 251 days.

(21) Appl. No.: 16/758,026

(22) PCT Filed: Oct. 31, 2019

(86) PCT No.: PCT/CN2019/114647
§ 371 (c)(1),
(2) Date: Apr. 21, 2020

(87) PCT Pub. No.: WO2020/140599
PCT Pub. Date: Jul. 9, 2020

(65) Prior Publication Data
US 2021/0204902 A1    Jul. 8, 2021

(30) Foreign Application Priority Data
Jan. 2, 2019 (CN) .......................... 201910001236.X (51) Int. Cl.
*A61B 7/02* (2006.01)
*A61B 7/04* (2006.01)

(52) U.S. Cl.
CPC ................ *A61B 7/026* (2013.01); *A61B 7/04* (2013.01); *A61B 2562/0204* (2013.01); *A61B 2562/046* (2013.01)

(58) Field of Classification Search
CPC ... A61B 7/026; A61B 7/04; A61B 2562/0204; A61B 2562/046
See application file for complete search history.

(56) References Cited

U.S. PATENT DOCUMENTS 9,955,939 B2 * 5/2018 Sezan ...................... A61B 7/00
2011/0222697 A1    9/2011 Dong et al.
(Continued)

FOREIGN PATENT DOCUMENTS

CN    102149329 A    8/2011
CN    102271589 A    12/2011
(Continued)

OTHER PUBLICATIONS

ISA China National Intellectual Property Administration, International Search Report Issued in Application No. PCT/CN2019/114647, WIPO, 18 pages. (Submitted with Partial Translation).
(Continued)

*Primary Examiner* — Andrew L Sniezek
(74) *Attorney, Agent, or Firm* — McCoy Russell LLP (57) ABSTRACT

The present disclosure provides a heart sound monitoring device and a method for acquiring a heart sound signal. The heart sound monitoring device of the present disclosure includes: a plurality of heart sound sensors, configured to correspond to different heart sound auscultation positions in a region to be monitored and be capable of collecting vibration signals generated when the different heart sound
(Continued)

auscultation positions are vibrated; and a heart sound locator, configured to determine a primary heart sound sensor and a secondary heart sound sensor in the plurality of heart sound sensors according to characteristics of the vibration signals collected by the plurality of heart sound sensors.

20 Claims, 5 Drawing Sheets

(56) References Cited

U.S. PATENT DOCUMENTS

| | | |
|---|---|---|
| 2011/0257548 A1 | 10/2011 | Dong et al. |
| 2012/0209131 A1 | 8/2012 | Jones et al. |
| 2014/0378849 A1 | 12/2014 | Krimsky et al. |
| 2017/0215835 A1 | 8/2017 | Sezan et al. |

FOREIGN PATENT DOCUMENTS

| | | |
|---|---|---|
| CN | 102512154 A | 6/2012 |
| CN | 205041431 U | 2/2016 |
| CN | 106175751 A | 12/2016 |
| CN | 108378843 A | 8/2018 |
| CN | 108392220 A | 8/2018 |
| CN | 108601577 A | 9/2018 |
| CN | 108710108 A | 10/2018 |
| CN | 108784679 A | 11/2018 |
| CN | 109498054 A | 3/2019 |

OTHER PUBLICATIONS

State Intellectual Property Office of the People's Republic of China, Office Action and Search Report Issued in Application No. 201910001236.X, dated Mar. 3, 2020, 27 pages. (Submitted with Partial Translation).

* cited by examiner

HEART SOUND MONITORING DEVICE AND METHOD FOR ACQUIRING HEART SOUND SIGNAL

CROSS-REFERENCE TO RELATED APPLICATIONS

The present application is a U.S. National Phase of International Application No. PCT/CN2019/114647, entitled "HEART SOUND MONITORING DEVICE AND METHOD FOR ACQUIRING HEART SOUND SIGNAL", and filed on Oct. 31, 2019. International Application No. PCT/CN2019/114647 claims priority to Chinese Patent Application No. 201910001236.X filed on Jan. 2, 2019. The entire contents of each of the above-listed applications are hereby incorporated by reference for all purposes.

TECHNICAL FIELD

The present disclosure relates to the technical field of detection equipment, in particular, to a heart sound monitoring device and a method for acquiring a heart sound signal.

BACKGROUND

At present, the existing heart sound detector is generally a handheld device. During the auscultation process, the auscultation head of the heart sound detector must be continuously moved manually to obtain heart sounds at different positions and to determine the best auscultation position in each auscultation region.

SUMMARY

An object of the present disclosure is to provide a heart sound monitoring device and a method for acquiring a heart sound signal.

An embodiment of the present disclosure provides a heart sound monitoring device, including:
  a plurality of heart sound sensors, configured to correspond to different heart sound auscultation positions in a region to be monitored and be capable of collecting vibration signals generated when the different heart sound auscultation positions are vibrated; and
  a heart sound locator, configured to determine a primary heart sound sensor and a secondary heart sound sensor in the plurality of heart sound sensors according to characteristics of the vibration signals collected by the plurality of heart sound sensors.

In an embodiment, the heart sound monitoring device includes at least one sensor dense distribution region and a sensor sparse distribution region surrounding the sensor dense distribution region, and a distribution density of the heart sound sensors located in the sensor dense distribution region is greater than a distribution density of the heart sound sensors located in the sensor sparse distribution region.

In an embodiment, in the heart sound monitoring device, an area of a vibration sensing region of the heart sound sensor located in the sensor dense distribution region is smaller than an area of a vibration sensing region of the heart sound sensor located in the sensor sparse distribution region.

In an embodiment, in the heart sound monitoring device, the area of the vibration sensing region of the heart sound sensor located in the sensor dense distribution region is in a range of 1 cm$^2$ to 1.5 cm$^2$, and the area of the vibration sensing region of the heart sound sensor located in the sensor sparse distribution region is in a range of 2 cm$^2$ to 3 cm$^2$.

In an embodiment, in the heart sound monitoring device, a shape of a peripheral contour of the sensor dense distribution region is a shape of a projection of the heart on a plane.

In an embodiment, in the heart sound monitoring device, the plurality of heart sound sensors has an identical area of a vibration sensing region and is arranged uniformly in an array.

In an embodiment, in the heart sound monitoring device, the plurality of heart sound sensors is linked as an entirety through a flexible material.

In an embodiment, in the heart sound monitoring device, the heart sound locator is configured to:
  acquire the vibration signals collected by the plurality of heart sound sensors within a first preset period of time;
  calculate heart sound envelopes corresponding to the vibration signals collected by the plurality of heart sound sensors at a plurality of time points within the first preset period of time;
  calculate heart sound components corresponding to the plurality of heart sound sensors and spectrum information about the heart sound components according to the heart sound envelopes corresponding to the plurality of heart sound sensors; and
  determine, in the spectrum information about the heart sound components corresponding to the plurality of heart sound sensors, at least one heart sound sensor corresponding to a heart sound component having a center frequency point whose difference from the preset center frequency point of the region to be monitored falls within a preset numerical range and having the highest spectral energy, as the primary heart sound sensor.

In an embodiment, in the heart sound monitoring device, the heart sound locator is further configured to determine a preset number of heart sound sensors surrounding the primary heart sound sensor as the secondary heart sound sensor.

In an embodiment, the heart sound monitoring device further includes a heart sound analyzer, which is configured to:
  acquire the vibration signals collected by the primary heart sound sensor and the secondary heart sound sensor within a second preset time period;
  calculate a signal average value of the vibration signals collected by the plurality of heart sound sensors included in the primary heart sound sensor and the secondary heart sound sensor at a preset time point within the second preset period of time, a plurality of the preset time points being provided and each of the plurality of preset time points corresponding to one of the signal average value;
  calculate heart sound envelopes corresponding to the signal average value;
  calculate heart sound components corresponding to the signal average value and spectrum information about the heart sound components according to the heart sound envelopes corresponding to the signal average value; and
  compare the spectrum information about the heart sound components with preset standard spectrum information corresponding to the region to be monitored, and acquire the heart sound signal of the region to be monitored according to a comparison result.

In an embodiment, the heart sound monitoring device further includes a displayer, which is configured to display the heart sound signal of the region to be monitored in a graphic or curve form.

An embodiment of the present disclosure also provides a method for acquiring a heart sound signal by configuring a heart sound monitoring device including a plurality of heart sound sensors and a heart sound locator, the method including:

providing a plurality of heart sound sensors at different heart sound auscultation positions in the region to be monitored, and acquiring vibration signals generated when the different heart sound auscultation positions are vibrated and collected by the plurality of heart sound sensors; and using the heart sound locator to determine a primary heart sound sensor for heart sound monitoring in the region to be detected and a preset number of a secondary heart sound sensors surrounding the primary heart sound sensor in the plurality of heart sound sensors according to characteristics of the vibration signals collected by the plurality of heart sound sensors.

In an embodiment, in the method for acquiring the heart sound signal, the heart sound monitoring device further includes a heart sound analyzer, and the method further includes:

using a heart sound analyzer to monitor vibration signals of the primary heart sound sensor and the secondary heart sound sensor;

calculating a signal average value of vibration signals collected by the plurality of heart sound sensors included in the primary heart sound sensor and the secondary heart sound sensors; and determining a heart sound signal corresponding to the region to be monitored according to the signal average value.

In an embodiment, in the method for acquiring the heart sound signal, when a plurality of heart sound sensors are provided at different heart sound auscultation positions in the region to be monitored, the plurality of heart sound sensors is arranged in a preset arrangement mode, and the arrangement mode includes:

allowing the plurality of heart sound sensors to have an identical area of a vibration sensing region and to be arranged uniformly in an array; or allowing the plurality of heart sound sensors to comprise at least one sensor dense distribution region and a sensor sparse distribution region surrounding the sensor dense distribution region, an area of the vibration sensing region of the heart sound sensor located in the sensor dense distribution region being smaller than an area of the vibration sensing region of the heart sound sensor located in the sensor sparse distribution region, and a distribution density of the heart sound sensors located in the sensor dense distribution region being greater than a distribution density of the heart sound sensors located in the sensor sparse distribution region.

In an embodiment, in the method for acquiring the heart sound signal, the step of using the heart sound locator to determine a primary heart sound sensor and a secondary heart sound sensor in the plurality of heart sound sensors includes:

acquiring the vibration signals collected by the plurality of heart sound sensors within a first preset period of time;

calculating heart sound envelopes corresponding to the vibration signals collected by the plurality of heart sound sensors at a plurality of time points within the first preset period of time;

calculating heart sound components corresponding to the plurality of heart sound sensors and spectrum information about the heart sound components according to the heart sound envelopes corresponding to the plurality of heart sound sensors; and determining, in the spectrum information about the heart sound components corresponding to the plurality of heart sound sensors, at least one heart sound sensor corresponding to a heart sound component having a center frequency point whose difference from the preset center frequency point of the region to be monitored falls within a preset numerical range and having the highest spectral energy, as the primary heart sound sensor.

In an embodiment, in the method for acquiring the heart sound signal, using the heart sound analyzer to monitor vibration signals of the primary heart sound sensor and the secondary heart sound sensor and determining the heart sound signal of the region to be monitored include:

acquiring the vibration signals collected by the primary heart sound sensor and the secondary heart sound sensor within a second preset period of time;

calculating a signal average value of the vibration signals collected by the plurality of heart sound sensors included in the primary heart sound sensor and the secondary heart sound sensor at a preset time point within the second preset period of time, a plurality of the preset time points being provided and each of the plurality of preset time points corresponding to one of the signal average value;

calculating heart sound envelopes corresponding to the signal average value;

calculating heart sound components corresponding to the signal average value and spectrum information about the heart sound components according to the heart sound envelopes corresponding to the signal average value; and comparing the spectrum information about the heart sound components with preset standard spectrum information corresponding to the region to be monitored, and acquire a heart sound signal corresponding to the region to be monitored.

DETAILED DESCRIPTION

The technical problems, the technical solutions, and the advantages of the present invention will be more clearly described in combination with the drawings and specific embodiments.

In the related art, the heart sound detector is usually a handheld device, and the heart sounds of different positions are acquired by manually moving the auscultation head. Therefore, the auscultation process is not easy to operate and takes a relatively long time, and thus it may cause auscultation errors, and cannot adapt to long-term heart sound monitoring and telemedicine. In order to solve the problem in the related art that the stethoscope needs to manually find and determine the best auscultation position and the auscultation process is not easy to operate, an embodiment of the present disclosure provides a heart sound monitoring device by providing a plurality of heart sound sensor capable of collecting vibration signals generated when the heart sound auscultation position is vibrated, and by using the heart sound locator to determine the primary heart sound sensor and the secondary heart sound sensor in the heart sound sensor according to the vibration signal collected by the heart sound sensor, thereby being capable of determining the best auscultation position during auscultation, and avoiding the problems that the manual auscultation of the best auscultation position cause the auscultation process to be not easy to operate and to be cumbersome.

Figure 1:
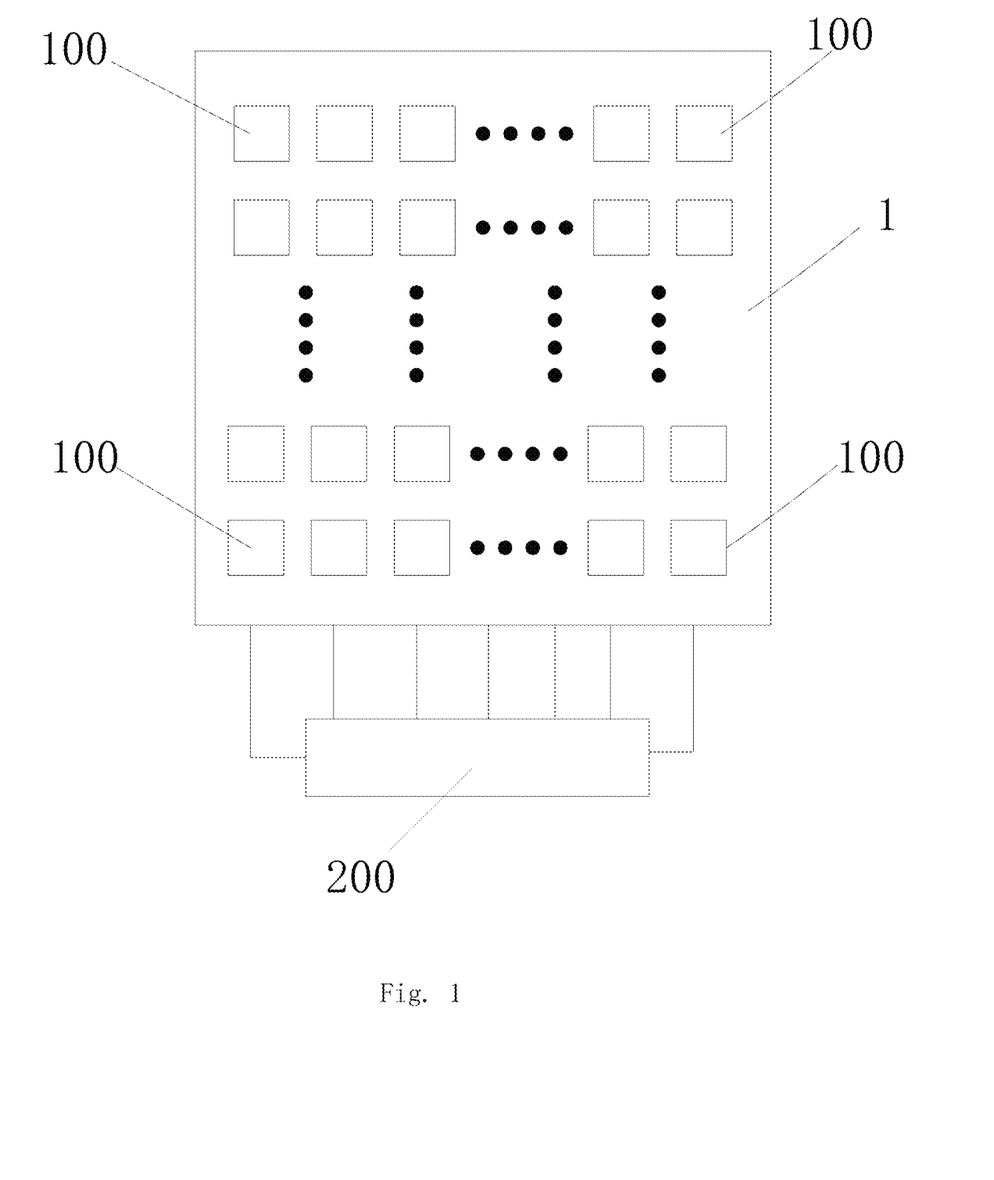
FIG. 1 is a schematic view showing a first implementation of a heart sound monitoring device according to an embodiment of the present disclosure.

FIGS. 1 to 6 are schematic views showing a heart sound monitoring device according to an embodiment of the present disclosure. As shown in FIG. 1, a heart sound monitoring device provided by an embodiment of the present disclosure includes:

a plurality of heart sound sensors 100, configured to correspond to different heart sound auscultation positions in a region to be monitored and be capable of collecting vibration signals generated when the different heart sound auscultation positions are vibrated; and a heart sound locator 200, connected to each heart sound sensor 100 and configured to determine a primary heart sound sensor and a secondary heart sound sensor in the plurality of heart sound sensors 100 according to characteristics of the vibration signals collected by the plurality of heart sound sensors 100.

When applied to heart sound monitoring, the heart sound monitoring device provided in this embodiment attaches the heart sound sensor to the position corresponding to the heart on the surface of the human or animal body, and the heart sound locator is capable of determining the primary heart sound sensor and the secondary heart sound sensor of the heart sound sensor according to the vibration signal collected by the heart sound sensor, thereby being capable of determining the best auscultation position during auscultation.

In the embodiment of the present disclosure, the heart sound sensor 100 may be a piezoelectric thin film sensor. The piezoelectric thin film sensor has excellent piezoelectric properties and a thickness ranging from 20 μm to 200 μm. When the piezoelectric thin film sensor is closely attached to the surface of the human body, due to the vibration of the body surface caused by the heart sound, the piezoelectric thin film sensor is capable of sensing the force of the vibration, to cause deformation and induce a charge on the surface. In addition, due to the periodic vibration of the heart sound, the piezoelectric thin film sensor can generate an alternating current signal, and thus it is possible to acquire vibration signals generated when the auscultation position of the heart sound is vibrated by acquiring the electrical signal generated by the piezoelectric thin film sensor. In addition, since the piezoelectric thin film sensor is capable of being attached to the surface of a human body surface to acquire vibration signals, heart sound monitoring with the piezoelectric thin film sensor is capable of preventing external noise interference, and the heart sound monitoring device has relatively high signal-to-noise ratio and sensitivity.

Figure 2:
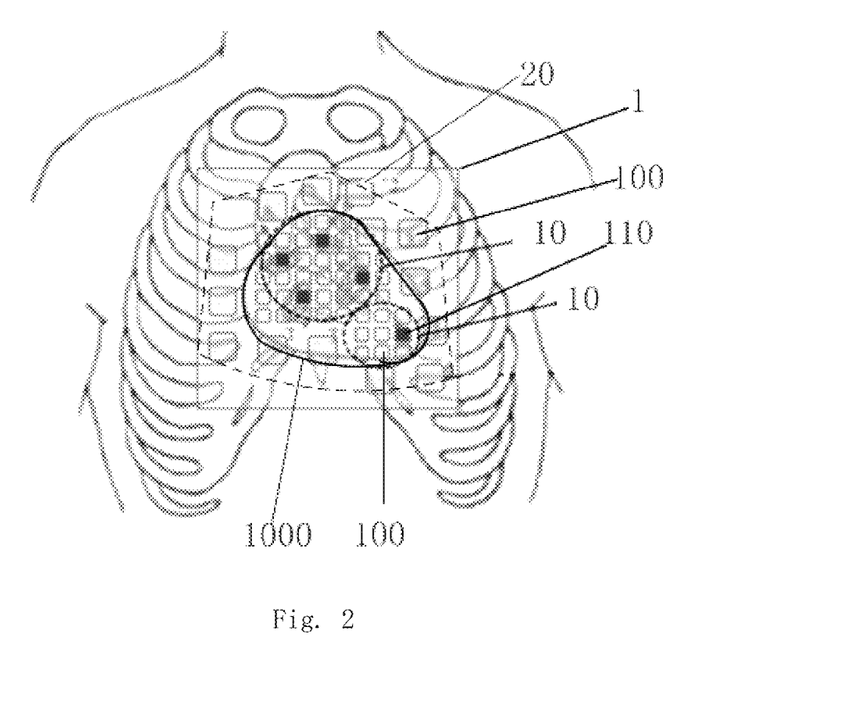
FIG. 2 is a schematic view showing a second implementation of a heart sound monitoring device according to an embodiment of the present disclosure.

In an embodiment, as shown in FIG. 2, the heart sound monitoring device provided by an embodiment of the present disclosure may include at least one sensor dense distribution region 10 and a sensor sparse distribution region 20 surrounding the sensor dense distribution region 10. A plurality of heart sound sensors 100 are respectively arranged in the sensor dense distribution region 10 and the sensor sparse distribution region 20, and the distribution density of the heart sound sensors 100 in the sensor dense distribution region 10 is greater than the distribution density of the heart sound sensors 100 in the sensor sparse distribution region 20.

In the above manner, the heart sound sensor is provide to include a sensor dense distribution region and a sensor sparse distribution region, and the sensor sparse distribution region is provide to surround the sensor dense distribution region, thereby avoiding excessive amounts of data and calculations and being capable of reducing the manufacturing cost while ensuring that the heart sound monitoring device is universal for different sized hearts.

As shown in FIG. 2, when the heart sound monitoring device includes at least one sensor dense distribution region 10 and a sensor sparse distribution region 20 surrounding the sensor dense distribution region 10, the area of the vibration sensing region of the heart sound sensor 100 located in the sensor dense distribution region 10 is smaller than the area of the vibration sensing region of the heart sound sensor 100 located in the sensor sparse distribution region 20.

In the above manner, making the area of the vibration sensing region of the heart sound sensor 100 located in the sensor dense distribution region 10 to be smaller than the area of the vibration sensing region of the heart sound sensor 100 located in the sparse distribution region 20 is capable of ensuring the sensitivity and detection accuracy of the vibration signal monitoring of heart sounds in the region to be detected.

Exemplarily, the area of the vibration sensing region of the heart sound sensor 100 located in the sensor dense distribution region 10 may be in a range of 1 cm$^2$ to 1.5 cm$^2$, and the area of the vibration sensing region of the heart sound sensor 100 located in the sensor sparse distribution region 20 may be in a range of 2 cm$^2$ to 3 cm$^2$.

In addition, exemplarily, each heart sound sensor 100 located in the sensor sparse distribution region 20 may correspond to two to three heart sound sensors 100 located in the sensor dense distribution region 10. That is, two to three heart sound sensors 100 located in the sensor dense distribution region 10 are distributed in the sensor sparse distribution region 20 and at the periphery of the heart sound sensor 100 located at the edges.

Based on the above manner, as compared with the heart sound sensor 100 in the sensor sparse distribution region 20, the heart sound sensor 100 in the sensor dense distribution region 10 has a larger distribution density and a smaller vibration sensing region, is capable of increasing the sensing sensitivity of the heart sound sensor 100 located in the sensor dense distribution region 10, ensures the accuracy of the data obtained by sensing, and is capable of reducing the overall number of the heart sound sensor 100, thereby reducing the cost and the amount of data processing while ensuring versatility.

In an embodiment, as shown in FIG. 2, in the heart sound monitoring device provided by the embodiment of the present disclosure, a shape of a peripheral contour of the sensor dense distribution region 10 may be a shape 1000 of a projection of a heart on a plane. That is, the shape of the peripheral contour formed by the sensor dense distribution region 10 is the same as the shape 1000 of the projection of the heart in the region to be detected, and the area of the region included by the peripheral contour of the sensor dense distribution region 10 is greater than or equal to the area of the planar projection shape 1000 of the heart on the heart sound monitoring device.

By setting the shape of the dense distribution region of the sensor according to the shape of the planar projection of the heart, the vibration signal of the heart sound in the region to be detected is capable of being detected by the heart sound monitoring device. Thus excessive amounts of data and calculations are avoided and the manufacturing cost is reduced.

In the above manner, as shown in FIG. 2, the heart sound sensors 100 can be densely arranged at positions corresponding to the heart, and the heart sound sensors 100 can be sparsely arranged at positions corresponding to the periphery of the heart. As can be understood, for the normal human, the size of a heart is same as that of a fist, so the region surrounded by the combination of the plurality of heart sound sensors 100 can be set into a square with a side length of 10 to 15 cm or other shapes with equivalent dimensions. The approximate center of the region surrounded by the plurality of heart sound sensors 100 is a sensor dense distribution region 10, and a plurality of heart sound sensors 100 equally spaced and having an area of a vibration sensing region of 1 $cm^2$ to 1.5 $cm^2$ is arranged in the sensor dense distribution region 10. Exemplarily, the peripheral contour shape of the sensor dense distribution region 10 is same as the planar projection shape 1000 of the heart, and the planar projection shape 1000 of the heart on the plane where the heart sound sensor 100 is located falls within the peripheral contour range formed by the sensor dense distribution region 10, or coincide with the peripheral contour range.

In the heart sound monitoring device provided by the embodiment of the present disclosure, the number of the sensor dense distributions 10 may be at least two. When the number of sensor dense distribution regions 10 is at least two, the peripheral contour shape formed by combining all the sensor dense distribution regions 10 is the same as the planar projection shape 1000 of the heart, and the planar projection shape 1000 of the heart falls within the peripheral contour range formed by combining all the sensor dense distribution regions 10, or coincides with the peripheral contour range.

It should be noted that the planar projection shape of the heart mentioned in the present disclosure refers to the shape formed by the orthogonal projection of the heart on the plane where the heart sound sensor is located.

Figure 3:
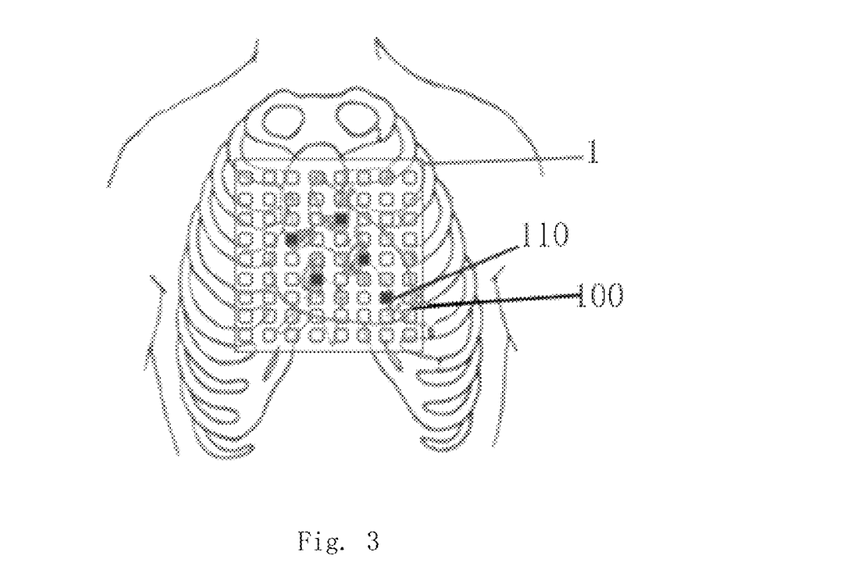
FIG. 3 is a schematic view showing a third implementation of a heart sound monitoring device according to an embodiment of the present disclosure.

In the heart sound monitoring device provided by the embodiment of the present disclosure, the arrangement of the plurality of heart sound sensors 100 is not limited to the above manner. As shown in FIG. 3, the plurality of heart sound sensors 100 has an identical area of a vibration sensing region and is arranged uniformly in an array.

In the heart sound monitoring device provided by the embodiment of the present disclosure, the plurality of heart sound sensors may be linked as an entirety through a flexible material, for the convenience of use.

In an embodiment, as shown in FIG. 1, a plurality of heart sound sensors 100 included in the heart sound monitoring device may be arranged on a flexible substrate 1 and linked as an entirety through the substrate 1. When the substrate 1 is attached to the human chest, the substrate 1 is attached to the human chest, and a plurality of heart sound sensors 100 respectively correspond to different parts of the human chest, in which each heart sound sensor 100 is capable of monitoring the vibration signals generated by the corresponding heart sound auscultation position during vibration.

In addition, the substrate 1 on which a plurality of heart sound sensors 100 are provided may be in an integral form, or may be in a form including a plurality of separates. That is, a part of the heart sound sensor 100 can be provided on one substrate, and the other part of the heart sound sensor 100 can be provided on another substrate. When a plurality of separates of the substrate is spliced and placed on a human chest, the plurality of heart sound sensors can be configured to detect vibration signals at different heart sound auscultation locations.

Figure 4:
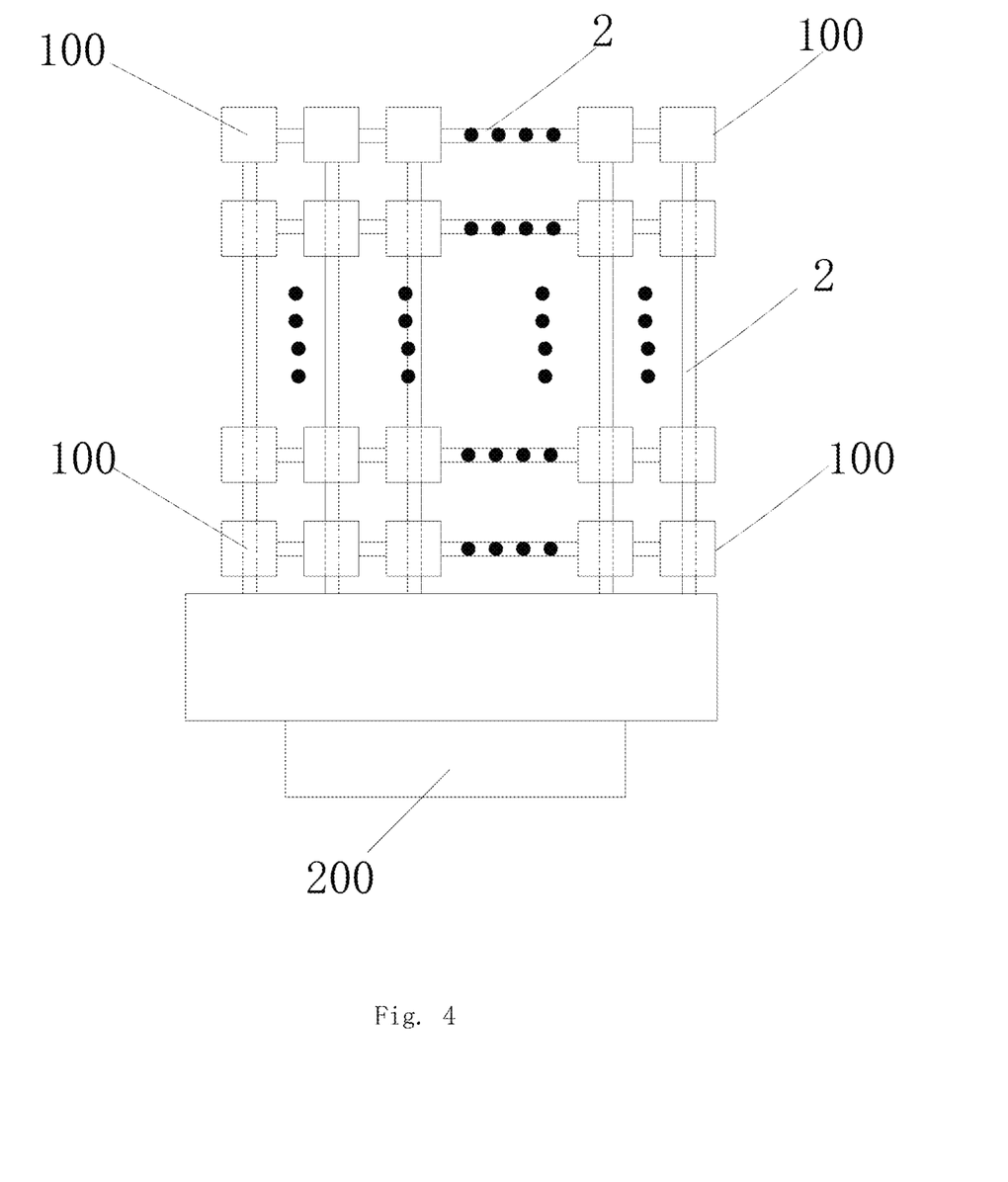
FIG. 4 is a schematic view showing a fourth implementation of a heart sound monitoring device according to an embodiment of the present disclosure.

In addition, as a manner for linking the plurality of heart sound sensors 100 as an entirety, as long as the plurality of heart sound sensors 100 can be linked together by a flexible material, the flexible material is not limited to be formed into a sheet-like substrate form, and may also be formed into another structure form. For example, in an example, as shown in FIG. 4, the flexible material may be a strip-shaped flexible material 2, thereby linking the plurality of heart sound sensors 100 into a plurality of strip-shaped structures.

Based on the above different linking manners of the heart sound sensor 100, when the separation distance between adjacent heart sound sensors 100 on the substrate 1 or other flexible materials is different, different distribution densities can be formed correspondingly. For example, as shown in FIG. 2, a plurality of heart sound sensors 100 may be combined to form a sensor dense distribution region 10 and a sensor sparse distribution region 20 surrounding the sensor dense distribution region 10.

In addition, as shown in FIG. 3, a plurality of heart sound sensors 100 can be linked into an entirety through a flexible substrate 1, and the plurality of heart sound sensors 100 are evenly arranged in an array on one surface of the substrate 1, in which each heart sound sensor 100 has an identical area of a vibration sensing region. When the flexible substrate 1 is attached to the human chest, the substrate 1 is attached to the human chest, and a plurality of heart sound sensors 100 respectively correspond to different parts of the human chest, in which each heart sound sensor 100 is capable of monitoring the vibration signals generated by the corresponding heart sound auscultation position during vibration.

Regarding the heart sound monitoring device provided in the embodiment of the present disclosure, since a plurality of heart sound sensors 100 are linked into an entirety through a flexible material, when applied to heart sound monitoring, only a plurality of heart sound sensors 100 linked as an entirety need to be attached to the chest and different heart sound sensors 100 are located at different heart sound auscultation positions in the region to be monitored, so that the heart sound locator is capable of automatically determining the primary heart sound sensor and the secondary heart sound sensor in the plurality of heart sound sensors corresponding to the region to be monitored, and the primary heart sound sensor and the secondary heart sound sensor is capable of monitoring heart sound. The heart sound monitoring device provided by the embodiment of the present disclosure avoids manual position adjustment of the heart sound monitoring position, is convenient to operate, and is capable of adapting to long-term heart sound monitoring and telemedicine.

It should be noted that the heart sound auscultation is divided into five regions medically, which are mitral valve region (M), pulmonary valve region (P), aortic valve region (A), aortic valve second auscultation region (Erb), and tricuspid valve region (T). The heart sound monitoring device provided by the embodiment of the present disclosure is capable of monitoring the entire region of a human chest or heart. That is, the region to be monitored is the entire region of the human chest or heart. In addition, according to the vibration signals generated by the plurality of heart sound sensors when it is vibrated at different heart sound auscultation positions, the heart sound locator is capable of determining the primary heart sound sensor and the secondary heart sound sensor of any one of the five heart sound auscultation regions corresponding to the human chest to be monitored.

Regarding the heart sound monitoring device provided by the embodiment of the present disclosure, when applied to heart sound monitoring so as to attach a plurality of heart sound sensors to the position of the body surface of a human or animal corresponding to the heart, the primary heart sound sensor is located at the position where the vibration of the corresponding heart is the strongest, so that it is capable of detecting the strongest vibration signal in the region to be monitored, and accurately acquiring the heart sound state of the region to be monitored. In addition, the vibration signal of the region to be monitored detected by the secondary heart sound sensor is slightly weaker than the vibration signal of the primary heart sound sensor, which can assist the primary heart sound sensor to achieve the heart sound state of the region to be monitored.

As can be understood, when the heart sound monitoring device includes at least one sensor dense distribution region and a sensor sparse distribution region surrounding the sensor dense distribution region, usually, the best auscultation region (i.e., the position of the primary heart sound sensor) is located in the sensor dense distribution region. That is, one of the heart sound sensors in the sensor dense distribution region is the primary heart sound sensor. Since the size of human heart varies in height and weight and the size of animal heart is more diverse, in the manufacturing heart sound monitoring devices, it is possible to correspondingly manufacture a heart sound monitoring device having sensor dense distribution regions of different sizes, and select an appropriate heart sound monitoring device according to the heart of the human or animal to be monitored, and ensure that the determined best auscultation region (i.e., the position of the primary heart sound sensor) is located within the sensor dense distribution region.

In the heart sound monitoring device provided by the embodiment of the present disclosure, the principle of the heart sound locator 200 capable of determining the primary heart sound sensor and the secondary heart sound sensor for heart sound monitoring in the region to be monitored is shown as follows:

corresponding to each heart sound auscultation region of the heart, different valves have different heart sound characteristics and energy. By taking the auscultation region of M as an example, the heart sound produced by the mitral valve is the high frequency component of the first heart sound (S1). Therefore, when the S1 high-frequency component of the heart sound collected by each heart sound sensor 100 is extracted, the position where the heart sound sensor 100 having the highest energy component is defined as the best auscultation position of the M auscultation region, the heart sound sensor 100 is the primary heart sound sensor, and a preset number of heart sound sensors 100 located surrounding the primary heart sound sensor may be secondary heart sound sensors. The signal collected by the primary heart sound sensor is set to SM, and the signal collected by its surrounding secondary heart sound sensors is set to SM1 to SMn. SM and SM1 to SMn together form a signal group that constitutes the M auscultation region, and are capable of further acting as the monitoring of heart sound state in auscultation region.

Based on the above principle, when the heart sound locator 200 determines the primary heart sound sensor and the secondary heart sound sensor in the plurality of heart sound sensors 100 according to the characteristics of the vibration signals collected by the plurality of heart sound sensors 100, this step specifically includes:

acquiring the vibration signals collected by the plurality of heart sound sensors 100 within a first preset period of time;

calculating heart sound envelopes corresponding to the vibration signals 100 collected by the plurality of heart sound sensors at a plurality of time points within the first preset duration;

culating heart sound components corresponding to the plurality of heart sound sensors 100 and spectrum information about the heart sound components according to the heart sound envelopes corresponding to the plurality of heart sound sensors 100; and determining, in the spectrum information about the heart sound components corresponding to the plurality of heart sound sensors 100, at least one heart sound sensor 100 corresponding to a heart sound component having a center frequency point whose difference from the preset center frequency point of the region to be monitored falls within a preset numerical range and having the highest spectral energy, as the primary heart sound sensor.

In the present disclosure, the first preset period of time refers to a preset time for the heart sound locator 200 to acquire heart sound vibration signals, which can be arbitrarily set according to actual conditions, for example, it can be set to 5 s to 1 min.

As can be understood, in the present disclosure, the heart sound locator 200 may be a central processing unit (CPU) or other modules having data storage and calculation functions.

For example, a specific method of determining a primary heart sound sensor and a secondary heart sound sensor in the plurality of heart sound sensors 100 may be performed as follows: acquiring the vibration signals collected by the plurality of heart sound sensors 100 within a first preset period of time (e.g., 10 s). The vibration signals collected by the plurality of heart sound sensors 100 is set to SM1~SMn, respectively, and Hilbert transform is used to calculate SM1~SMn at a plurality of time points (i.e., sampling time points) within the first preset period of time, corresponding to the heart sound envelope e(n), respectively.

Among them, the Hilbert transform is calculated as:

$$\hat{S}(t) = \int_{-\infty}^{+\infty} \frac{S(\tau)}{t-\tau} d\tau = S(t) \times \frac{1}{\pi t}.$$

Further, the calculation method corresponding to the heart sound envelope e(n) is:

$$e(n) = \sqrt{S^2(t) + \hat{S}^2(t)};$$

In the above formula, S(τ) is the vibration signal of any of SM1 to SMn at the sampling time point, t is the first preset period of time; S(t) is the vibration signal of any of SM1 to SMn, Ŝ(t) is the Hilbert transform value of S(t), that is, the value obtained by performing the convolution operation on S(t).

According to the above formula, the heart sound envelope e(n) corresponding to the vibration signal collected by each heart sound sensor can be calculated and obtained. That is, the heart sound envelopes e(n) corresponding to SM1 to SMn are calculated and obtained.

Further, the heart sound components corresponding to the plurality of heart sound sensors 100 and spectrum information about the heart sound components are calculated according to the heart sound envelopes e(n) corresponding to the plurality of heart sound sensors 100.

The method for above calculating heart sound components corresponding to the plurality of heart sound sensors 100 and spectrum information about the heart sound components specifically includes:

determining the maximum heart sound envelope value in the heart sound envelope e(n) corresponding to each heart sound sensor;

determining the value obtained by multiplying the maximum heart sound envelope value by the first value as a first threshold value, the first value being greater than or equal to 0.5 and less than 1;

determining a heartbeat cycle according to a time point of a plurality of heart sound envelopes e(n) that are greater than a first threshold of the heart sound envelopes e(n);

determining a first heart sound component and a second heart sound component according to a plurality of heart sound envelopes e(n) in one heartbeat cycle; and determining the spectrum information about the first heart sound component and the spectrum information about the second heart sound component by using Fourier transform according to the heart sound envelope e(n) corresponding to the first heart sound component and the second heart sound component.

For example, the above first value is 80%, and the value obtained by multiplying the maximum heart sound envelope value in the plurality of heart sound envelopes e(n) by the first value is the first threshold value. Among them, the determination criterion of the heart sound component is that a portion of a plurality of heart sound envelopes e(n) greater than 80% of the maximum heart sound envelope value (that is, a portion greater than the first threshold value) is the first heart sound component and the second heart sound component.

In addition, a value obtained by multiplying a maximum heart sound envelope value in a plurality of heart sound envelopes e(n) by a second value may be set as a second threshold value. The second value is greater than 0 and less than 0.5. For example, the second value may be set to 20%. The heart sound portions of the plurality of heart sound envelopes e(n) between the first threshold and the second threshold are other components (the third heart sound component, the fourth heart sound component, and other noises, etc.), and a portion of the plurality of heart sound envelopes e(n) that is less than the second threshold is noise interference.

The heartbeat period is determined according to the time points of the first heart sound component and the second heart sound component (that is, the heart sound envelope greater than the first threshold) in the plurality of heart sound envelopes e(n). Among them, if all the times that may be the first heart sound component and the second heart sound component can be regarded as a sequence T (i), the average value of T(2i+1)-T(2i−1) is approximately the heartbeat period.

Further, according to the rule that the time from the first heart sound component to the second heart sound component in one cycle is less than the time from the second heart sound to the first heart sound in the next cycle, the first heart sound component, the second heart sound component, the systolic and diastolic intervals can be distinguished. Further, Fourier transform can be used to quickly analyze the frequency components of the first heart sound component and the second heart sound component. Since the center frequencies of the sounds emitted by different valves are different, the best auscultation region can be determined according to the spectrum distributions of the first heart sound component and the second heart sound component.

Therefore, the above manner can obtain and analyze the first heart sound component and the second heart sound component in a plurality of heart sound envelopes e(n) in one heartbeat cycle. According to the heart sound envelope e(n) corresponding to the first heart sound component and the second heart sound component, Fourier transform can be used to determine the spectrum information about the first heart sound component and the spectrum information about the second heart sound component, and determine, in the spectrum information about the heart sound components corresponding to the plurality of heart sound sensors 100, at least one heart sound sensor corresponding to a heart sound component having a center frequency point whose difference from the preset center frequency point of the heart sound auscultation region corresponding to the region to be monitored falls within a preset numerical range and having the highest spectral energy, as the primary heart sound sensor, thereby determining the best auscultation region.

After the primary heart sound sensor is determined, the heart sound locator 200 may determine the secondary heart sound sensor corresponding to the primary heart sound sensor according to a predetermined correspondence relationship between the primary heart sound sensor and the secondary heart sound sensor surrounding the primary heart sound sensor.

As shown in FIG. 2 and FIG. 3, according to the above manner, the primary heart sound sensor 110 can be determined, and according to a predetermined correspondence relationship between the primary heart sound sensor and the surrounding secondary heart sound sensor, a preset number of heart sound sensors surrounding the primary heart sound sensor 110 can be determined as the secondary heart sound sensor. Among them, the preset number is not particularly limited, and can be arbitrarily set according to the actual situation, for example, it can be 1 to 20.

The heart sound monitoring device provided by the embodiment of the present disclosure can subject the obtained vibration signal data to noise reduction processing by determining the primary heart sound sensor capable of monitoring the heart sound state of the region to be monitored and the secondary heart sound sensor surrounding the primary heart sound sensor and by using the data of the vibration signal monitored by the secondary heart sound sensor, so that the accuracy of the obtained heart sound state can be guaranteed.

Figure 5:
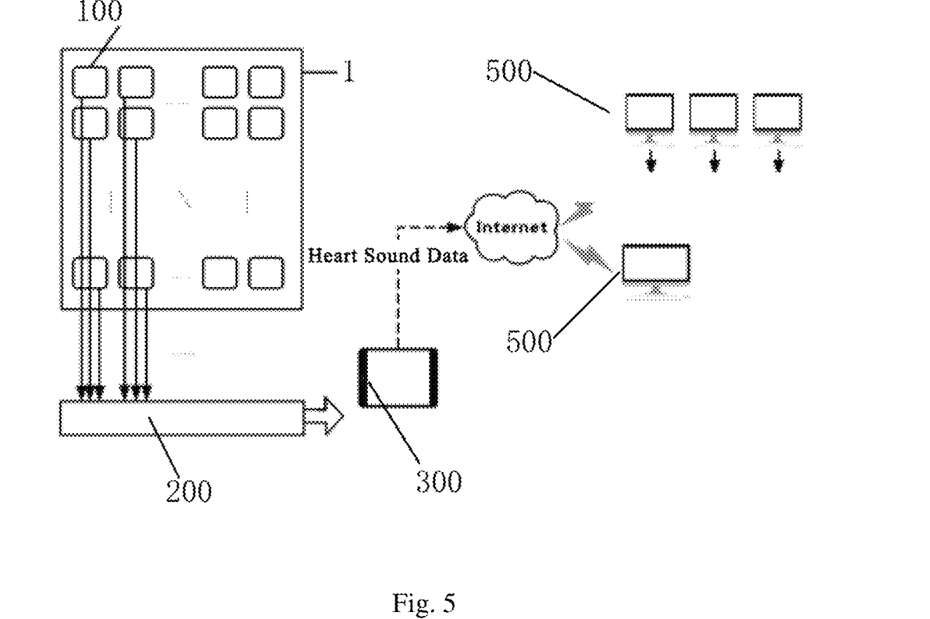
FIG. 5 is a schematic view showing a fifth implementation of a heart sound monitoring device according to an embodiment of the present disclosure.

In an example, as shown in FIG. 5, the heart sound monitoring device provided by the embodiment of the present disclosure may further include: a heart sound analyzer 300 connected to the heart sound locator 200, and the heart sound analyzer 300 is configured to:

monitor the vibration signals collected by the primary heart sound sensor and the secondary heart sound sensor within a second preset period of time; and acquire the heart sound signal of the region to be monitored according to the vibration signals collected by the primary heart sound sensor and the secondary heart sound sensor within a second preset period of time.

In the present disclosure, the second preset period of time refers to a preset time for the heart sound analyzer 300 to monitor the heart sound vibration signal, which can be arbitrarily set according to the actual situation, and is not particularly limited. For example, it can be set to be greater than or equal to 1 min, and can also be set to be less than or equal to 1 h.

As can be understood, in the present disclosure, the heart sound analyzer 300 may be a central processing unit (CPU) or other modules having data storage and calculation functions.

In the embodiment of the present disclosure, as shown in FIG. 5, each heart sound sensor 100 is connected to the heart sound locator 200 by a lead wire. When the vibration signal generated when the heart sound auscultation position is vibrated and collected by the heart sound sensor 100, the heart sound locator 200 is capable of converting the analog electrical signal output by the heart sound sensor 100 into a digital signal through an analog/digital converter, and is capable of storing the digital signals into the storage medium of the heart sound locator 200. Further, the heart sound locator 200 may determine the primary heart sound sensor and the secondary heart sound sensor according to the vibration signals collected by each heart sound sensor 100, and transmit the determined data to the heart sound analyzer 300 in a wireless or wired manner. As a transmission method, for example, the determined data is transmitted to the heart sound analyzer 300 by a micro universal serial bus (Micro USB) universal interface or a bluetooth low energy wireless interface.

In addition, the heart sound locator 200 can also transmit the data of the vibration signals collected by the primary heart sound sensor and the secondary heart sound sensor to the heart sound analyzer 300, so that the heart sound analyzer 300 is capable of monitoring the heart sound signal of the region to be monitored according to the vibration signals collected by the primary heart sound sensor and the secondary heart sound sensor within a second preset period of time.

Based on the settings of the above-mentioned heart sound monitoring device, the heart sound locator 200, according the data of the collected vibration signal of the plurality of heart sound sensors 100, locates the primary heart sound sensor of the region to be monitored, determines the position corresponding to the primary heart sound sensor as the best auscultation position, and determines the plurality of heart sound sensors 100 located surrounding the primary heart sound sensor as the secondary heart sound sensor, thereby completing the positioning of the heart sound sensor 100. After the heart sound locator 200 analyzes and determines the primary heart sound sensor and the secondary heart sound sensor, the heart sound analyzer 300 is capable of monitoring the vibration signals collected by the determined primary heart sound sensor and the secondary heart sound sensor within a second preset period of time to determine the heart sound signal.

Further, the heart sound analyzer 300 is in the heart sound real-time monitoring working state, so that only the data of the vibration signals collected by the primary heart sound sensor and the secondary heart sound sensor can be monitored, thereby reducing the amount of data and facilitating real-time transmission of the signal.

Exemplarily, the heart sound analyzer 300 determines the heart sound signal of the region to be monitored according to the vibration signals collected by the primary heart sound sensor and the secondary heart sound sensor within a second preset period of time, this step specifically includes:

calculating a signal average value of the vibration signals collected by the plurality of heart sound sensors included in the primary heart sound sensor and the secondary heart sound sensor at a preset time point within the second preset period of time, a plurality of the preset time points being provided and each of the plurality of preset time points corresponding to one of the average value signal;

calculating heart sound envelopes corresponding to each signal average value;

calculating heart sound components corresponding to the signal average value and spectrum information about the heart sound components according to the heart sound envelopes corresponding to the signal average value; and comparing the spectrum information about the heart sound components with preset standard spectrum information corresponding to the region to be monitored, and acquire the heart sound signal of the region to be monitored according to a comparison result.

Exemplarily, the above-mentioned specific manner of calculating the heart sound envelope corresponding to each signal average according to the signal average value as well as calculating heart sound components corresponding to the signal average value and spectrum information about the heart sound components according to the heart sound envelopes corresponding to the signal average value is same as the manner of calculating the heart sound envelope and calculating the spectrum information when the above-mentioned heart sound locator 200 determines the primary heart sound sensor, which will not be described herein again.

It should be understood that the above-mentioned preset standard frequency spectrum information is frequency spectrum information when the heart sound corresponding to the region to be monitored is healthy or normal. Comparing the spectrum information calculated according to the signal average value with preset standard spectrum information is capable of determining whether the heart sound state of the region to be monitored is normal or whether a lesion occurs.

The heart sound monitoring device of the embodiment of the present disclosure is capable of effectively eliminating the white noise in the vibration signal of the main heart sound sensor and improving the signal-to-noise ratio by using the signal average value of the vibration signals collected by the plurality of heart sound sensors included in the primary heart sound sensor and the secondary heart sound sensor as the signal data for determining the heart sound state of the region to be monitored.

Figure 6:
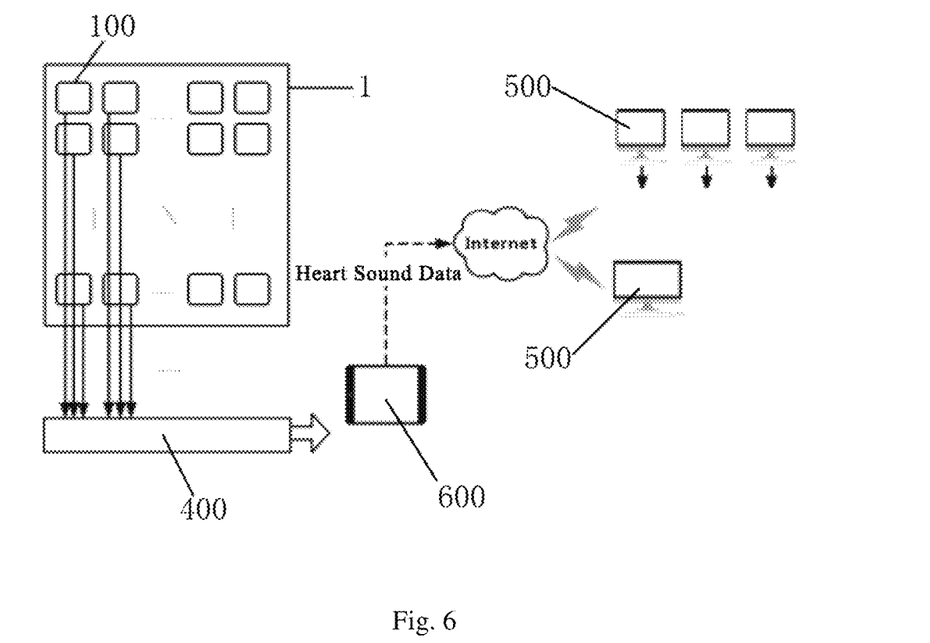
FIG. 6 is a schematic view showing a sixth implementation of a heart sound monitoring device according to an embodiment of the present disclosure.

In the heart sound monitoring device provided by the embodiment of the present disclosure, as shown in FIG. 6, the heart sound locator 200 and the heart sound analyzer 300 may also be integrated into a processor 600. In the heart sound monitoring device, each heart sound sensor 100 is connected to one signal collector 400 through a lead wire. The signal collector 400 is capable of converting an analog electrical signal output by the heart sound sensor 100 into a digital signal through an analog/digital converter, storing the converted digital signal in a storage medium of the signal collector 400, and transmitting the converted digital signal to the integrated processor 600 through a wireless or wired manner. The processor 600 determines the primary heart sound sensor and the secondary heart sound sensor in the plurality of heart sound sensors, and monitors the vibration signals collected by the primary heart sound sensor and the secondary heart sound sensor within a second preset period of time, thereby achieving the heart sound signal of the region to be monitored.

As can be understood, in the present disclosure, the processor 600 may be a central processing unit (CPU) or other modules having data storage and calculation functions.

In the heart sound monitoring device provided by the embodiment of the present disclosure, as shown in FIG. 5 and FIG. 6, the heart sound analyzer 300 or the processor 600 may further transmit the heart sound signal of the region to be monitored to the remote server 500 through the network. The remote server 500 may be, for example, a remote medical system of a hospital, and is used to achieve the purpose of remote medical treatment.

Regarding the heart sound monitoring device provided by the embodiment of the present disclosure, since the heart sound sensor 100 can be directly fixedly attached to the human chest for heart sound monitoring, after the preliminary positioning of the primary heart sound sensor and the secondary heart sound sensor of the region to be monitored during use, there is no need to operate the device, as long as the analyzed data obtained by the heart sound analyzer 300 is continuously monitor, and there is no problem that the manual operation of the auscultation process affects the monitoring result.

In an embodiment, the heart sound monitoring device provided by the embodiment of the present disclosure further includes a displayer, which is configured to display the heart sound signal of the region to be monitored in a graphic or curve form.

Specifically, the displayer may be connected to the heart sound analyzer 300 or the processor 600 and configured to acquire and display a heart sound signal output by the heart sound analyzer 300 or the processor 600.

Figure 7:
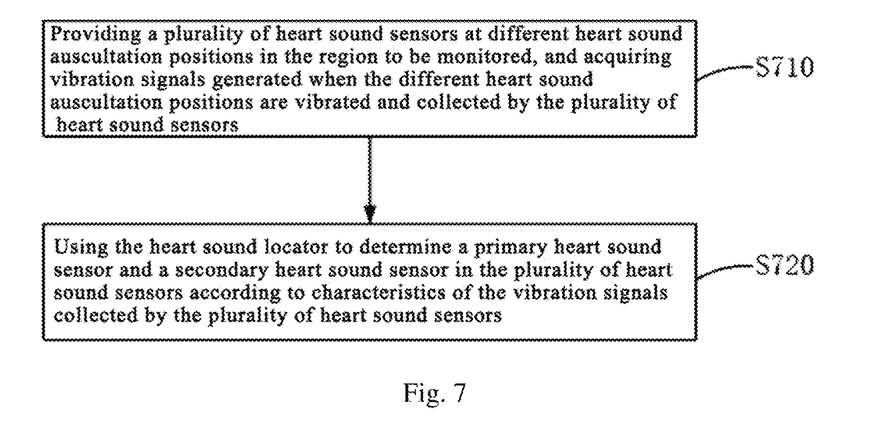
FIG. 7 is a schematic view showing a first implementation of a method for acquiring a heart sound signal according to an embodiment of the present disclosure.

An embodiment of the present disclosure also provides a method for acquiring a heart sound signal. As shown in FIG. 7, an embodiment of the present disclosure also provides a method for acquiring a heart sound signal by configuring a heart sound monitoring device including a plurality of heart sound sensors and a heart sound locator, the method including:

S710: providing a plurality of heart sound sensors at different heart sound auscultation positions in the region to be monitored, and acquiring vibration signals generated when the different heart sound auscultation positions are vibrated and collected by the plurality of heart sound sensors;

S720: using the heart sound locator to determine a primary heart sound sensor for heart sound monitoring in the region to be detected and a preset number of a secondary heart sound sensors surrounding the primary heart sound sensor in the plurality of heart sound sensors according to characteristics of the vibration signals collected by the plurality of heart sound sensors.

Specifically, in step S710, when a plurality of heart sound sensors are provided at different heart sound auscultation positions in the region to be monitored, the plurality of heart sound sensors is arranged in a preset arrangement mode, and the arrangement mode includes:

allowing the plurality of heart sound sensors to have an identical area of a vibration sensing region and to be arranged uniformly in an array; or allowing the plurality of heart sound sensors to comprise at least one sensor dense distribution region and a sensor sparse distribution region surrounding the sensor dense distribution region, an area of the vibration sensing region of the heart sound sensor located in the sensor dense distribution region being smaller than an area of the vibration sensing region of the heart sound sensor located in the sensor sparse distribution region, and a distribution density of the heart sound sensors located in the sensor dense distribution region being greater than a distribution density of the heart sound sensors located in the sensor sparse distribution region.

Specifically, in step S720, using the heart sound locator to determine a primary heart sound sensor and a secondary heart sound sensor in the plurality of heart sound sensors specifically includes:

acquiring the vibration signals collected by the plurality of heart sound sensors within a first preset period of time;

calculating heart sound envelopes corresponding to the vibration signals collected by the plurality of heart sound sensors at a plurality of time points within the first preset period of time;

calculating heart sound components corresponding to the plurality of heart sound sensors and spectrum information about the heart sound components according to the heart sound envelopes corresponding to the plurality of heart sound sensors; and determining, in the spectrum information about the heart sound components corresponding to the plurality of heart sound sensors, at least one heart sound sensor corresponding to a heart sound component having a center frequency point whose difference from the preset center frequency point of the region to be monitored falls within a preset numerical range and having the highest spectral energy, as the primary heart sound sensor.

Further, a preset number of heart sound sensors surrounding the primary heart sound sensor may be determined as the secondary heart sound sensors.

Based on the above manner, analyzing and calculating the vibration information collected by plurality of heart sound sensors located at different heart sound auscultation positions can determine the primary heart sound sensor and secondary heart sound sensor for heart sound detection in the region to be detected, and can provide a monitoring point for a further heart sound monitoring.

As for the specific manner of determining the primary heart sound sensor and the secondary heart sound sensor in the plurality of heart sound sensors, reference may be made to the detailed description on the heart sound monitoring device above, which will not be described herein again.

Figure 8:
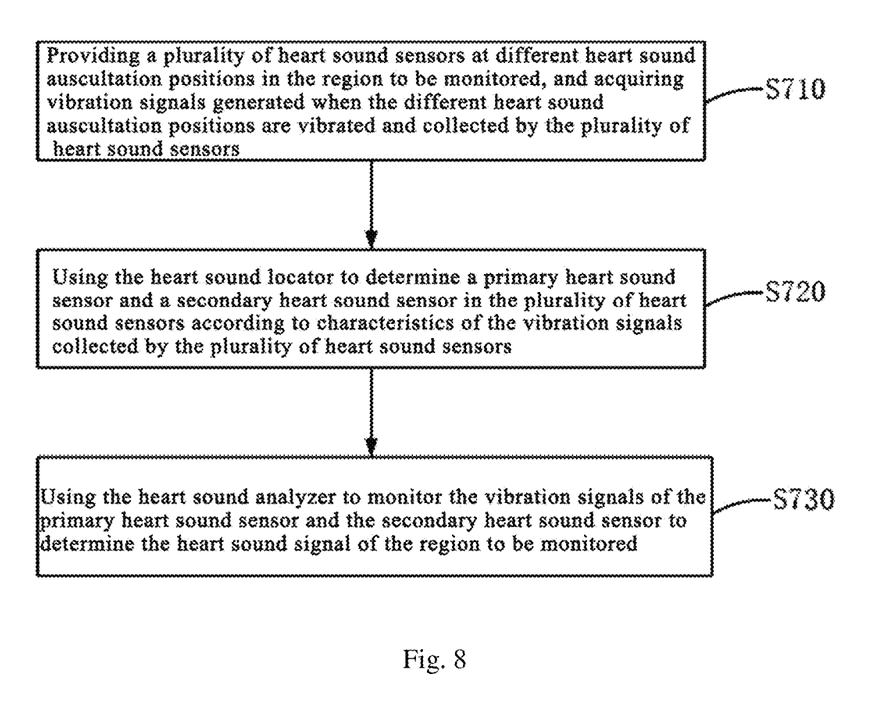
FIG. 8 is a schematic view showing a second implementation of a method for acquiring a heart sound signal according to an embodiment of the present disclosure.

In an embodiment, as shown in FIG. 8, in the method for acquiring the heart sound signal provided by an embodiment of the present disclosure, the heart sound monitoring device further includes a heart sound analyzer, and the method further includes S730:

using a heart sound analyzer to monitor vibration signals of the primary heart sound sensor and the secondary heart sound sensor;

calculating a signal average value of vibration signals collected by the plurality of heart sound sensors included in the primary heart sound sensors and the secondary heart sound sensors; and determining a heart sound signal of the region to be monitored according to the signal average value.

Specifically, in step S730, using a heart sound locator to monitor the vibration signals of the primary heart sound sensor and the secondary heart sound sensor to determine the heart sound signal of the region to be monitored, this step specifically includes:

acquiring the vibration signals collected by the primary heart sound sensors and the secondary heart sound sensors within a second preset period of time;

calculating a signal average value of the vibration signals collected by the plurality of heart sound sensors included in the primary heart sound sensors and the secondary heart sound sensors at a preset time point within the second preset period of time, a plurality of the preset time points being provided and each of the plurality of preset time points corresponding to one of the average value signal;

calculating heart sound envelopes corresponding to the signal average value;

calculating heart sound components corresponding to the signal average value and spectrum information about the heart sound components according to the heart sound envelopes corresponding to the signal average value; and comparing the spectrum information about the heart sound components with preset standard spectrum information corresponding to the region to be monitored, and acquiring a heart sound signal corresponding to the region to be monitored.

The above specific manner of calculating the heart sound envelope corresponding to each signal average value as well as calculating heart sound components corresponding to the signal average value and spectrum information about the heart sound components according to the heart sound envelopes corresponding to the signal average value, reference may be made to the detailed description on the heart sound monitoring device above, which will not be described herein again.

The method for achieving a heart sound signal provided by the embodiment of the present disclosure is capable of calculating and achieving the heart sound signal of the region to be monitored by further monitoring the vibration signals of the primary heart sound sensor and the secondary heart sound sensor of the region to be detected, and analyzing the vibration signals.

According to the above method for acquiring a heart sound signal, arranging the heart sound sensor in accordance with the above arrangement and allowing the heart sound analyzer and the heart sound locator to respectively have the above functions can allow the heart sound monitoring device including the above device parts to have the function of determining the best auscultation position during auscultation, and avoid the problems that the manual auscultation of the best auscultation position cause the auscultation process to be not easy to operate and to be cumbersome.

The above descriptions are optional embodiments of the present disclosure. It should be noted that one skilled in the art would make several improvements and substitutions without departing from the principles of the present disclosure. These improvements and modifications should also be regarded as the protection scope of the present disclosure.

The invention claimed is:

1. A heart sound monitoring device, comprising:

a plurality of heart sound sensors, configured to correspond to different heart sound auscultation positions in a region to be monitored and be capable of collecting vibration signals generated when the different heart sound auscultation positions are vibrated; and a heart sound locator, configured to determine a primary heart sound sensor and a secondary heart sound sensor in the plurality of heart sound sensors according to characteristics of the vibration signals collected by the plurality of heart sound sensors, wherein the heart sound monitoring device comprises at least one sensor dense distribution region and a sensor sparse distribution region surrounding the sensor dense distribution region, and a distribution density of the heart sound sensors located in the sensor dense distribution region is greater than a distribution density of the heart sound sensors located in the sensor sparse distribution region, wherein a shape of a peripheral contour of the sensor dense distribution region in the heart sound monitoring device is a shape of a projection of the heart on a plane.

2. The heart sound monitoring device of claim 1, wherein an area of a vibration sensing region of the heart sound sensor located in the sensor dense distribution region is smaller than an area of a vibration sensing region of the heart sound sensor located in the sensor sparse distribution region.

3. The heart sound monitoring device of claim 2, wherein the area of the vibration sensing region of the heart sound sensor located in the sensor dense distribution region is in a range of 1 $cm^2$ to 1.5 $cm^2$, and the area of the vibration sensing region of the heart sound sensor located in the sensor sparse distribution region is in a range of 2 $cm^2$ to 3 $cm^2$.

4. The heart sound monitoring device of claim 2, wherein the plurality of heart sound sensors is linked as an entirety through a flexible material.

5. The heart sound monitoring device of claim 3, wherein the plurality of heart sound sensors is linked as an entirety through a flexible material.

6. The heart sound monitoring device of claim 3, wherein the heart sound locator is configured to:

acquire the vibration signals collected by the plurality of heart sound sensors within a first preset period of time;

calculate heart sound envelopes corresponding to the vibration signals collected by the plurality of heart sound sensors at a plurality of time points within the first preset period of time;

calculate heart sound components corresponding to the plurality of heart sound sensors and spectrum information about the heart sound components according to the heart sound envelopes corresponding to the plurality of heart sound sensors; and determine, in the spectrum information about the heart sound components corresponding to the plurality of heart sound sensors, at least one heart sound sensor corresponding to a heart sound component having a center frequency point whose difference from the preset center frequency point of the region to be monitored falls within a preset numerical range and having the highest spectral energy, as the primary heart sound sensor.

7. The heart sound monitoring device of claim 1, wherein the plurality of heart sound sensors has an identical area of a vibration sensing region and is arranged uniformly in an array.

8. The heart sound monitoring device of claim 7, wherein the plurality of heart sound sensors is linked as an entirety through a flexible material.

9. The heart sound monitoring device of claim 7, wherein the heart sound locator is configured to:
acquire the vibration signals collected by the plurality of heart sound sensors within a first preset period of time;
calculate heart sound envelopes corresponding to the vibration signals collected by the plurality of heart sound sensors at a plurality of time points within the first preset period of time;
calculate heart sound components corresponding to the plurality of heart sound sensors and spectrum information about the heart sound components according to the heart sound envelopes corresponding to the plurality of heart sound sensors; and
determine, in the spectrum information about the heart sound components corresponding to the plurality of heart sound sensors, at least one heart sound sensor corresponding to a heart sound component having a center frequency point whose difference from the preset center frequency point of the region to be monitored falls within a preset numerical range and having the highest spectral energy, as the primary heart sound sensor.

10. The heart sound monitoring device of claim 1, wherein the plurality of heart sound sensors is linked as an entirety through a flexible material.

11. The heart sound monitoring device of claim 10, wherein the heart sound locator is configured to:
acquire the vibration signals collected by the plurality of heart sound sensors within a first preset period of time;
calculate heart sound envelopes corresponding to the vibration signals collected by the plurality of heart sound sensors at a plurality of time points within the first preset period of time;
calculate heart sound components corresponding to the plurality of heart sound sensors and spectrum information about the heart sound components according to the heart sound envelopes corresponding to the plurality of heart sound sensors; and
determine, in the spectrum information about the heart sound components corresponding to the plurality of heart sound sensors, at least one heart sound sensor corresponding to a heart sound component having a center frequency point whose difference from the preset center frequency point of the region to be monitored falls within a preset numerical range and having the highest spectral energy, as the primary heart sound sensor.

12. The heart sound monitoring device of claim 1, wherein the heart sound locator is configured to:
acquire the vibration signals collected by the plurality of heart sound sensors within a first preset period of time;
calculate heart sound envelopes corresponding to the vibration signals collected by the plurality of heart sound sensors at a plurality of time points within the first preset period of time;
calculate heart sound components corresponding to the plurality of heart sound sensors and spectrum information about the heart sound components according to the heart sound envelopes corresponding to the plurality of heart sound sensors; and
determine, in the spectrum information about the heart sound components corresponding to the plurality of heart sound sensors, at least one heart sound sensor corresponding to a heart sound component having a center frequency point whose difference from the preset center frequency point of the region to be monitored falls within a preset numerical range and having the highest spectral energy, as the primary heart sound sensor.

13. The heart sound monitoring device of claim 12, wherein the heart sound locator is further configured to determine a preset number of heart sound sensors surrounding the primary heart sound sensor as the secondary heart sound sensors.

14. The heart sound monitoring device of claim 13, wherein the heart sound monitoring device further comprises a heart sound analyzer, which is configured to:
acquire the vibration signals collected by the primary heart sound sensor and the secondary heart sound sensor within a second preset period of time;
calculate a signal average value of the vibration signals collected by the plurality of heart sound sensors comprised in the primary heart sound sensor and the secondary heart sound sensor at a preset time point within the second preset period of time, a plurality of preset time points being provided and each of the plurality of preset time points corresponding to one of the signal average value;
calculate heart sound envelopes corresponding to the signal average value;
calculate heart sound components corresponding to the signal average value and spectrum information about the heart sound components according to the heart sound envelopes corresponding to the signal average value; and
compare the spectrum information about the heart sound components with preset standard spectrum information corresponding to the region to be monitored, and acquire the heart sound signal of the region to be monitored according to a comparison result.

15. The heart sound monitoring device of claim 12, wherein the heart sound monitoring device further comprises a heart sound analyzer, which is configured to:
acquire the vibration signals collected by the primary heart sound sensor and the secondary heart sound sensor within a second preset period of time;
calculate a signal average value of the vibration signals collected by the plurality of heart sound sensors comprised in the primary heart sound sensor and the secondary heart sound sensor at a preset time point within the second preset period of time, a plurality of preset time points being provided and each of the plurality of preset time points corresponding to one of the signal average value;
calculate heart sound envelopes corresponding to the signal average value;
calculate heart sound components corresponding to the signal average value and spectrum information about the heart sound components according to the heart sound envelopes corresponding to the signal average value; and
compare the spectrum information about the heart sound components with preset standard spectrum information corresponding to the region to be monitored, and acquire the heart sound signal of the region to be monitored according to a comparison result.

16. The heart sound monitoring device of claim 15, wherein the heart sound monitoring device further comprises a displayer, which is configured to display the heart sound signal of the region to be monitored in a graphic or curve form.

17. A method for acquiring a heart sound signal by configuring a heart sound monitoring device comprising a plurality of heart sound sensors and a heart sound locator, the method comprising:
 providing a plurality of heart sound sensors at different heart sound auscultation positions in the region to be monitored, and acquiring vibration signals generated when the different heart sound auscultation positions are vibrated and collected by the plurality of heart sound sensors; and
 using the heart sound locator to determine a primary heart sound sensor for heart sound monitoring in the region to be detected and a preset number of a secondary heart sound sensors surrounding the primary heart sound sensor in the plurality of heart sound sensors according to characteristics of the vibration signals collected by the plurality of heart sound sensors,
 wherein the heart sound monitoring device further comprises a heart sound analyzer, and the method further comprises:
  using a heart sound analyzer to monitor vibration signals of the primary heart sound sensor and the secondary heart sound sensor;
  calculating a signal average value of vibration signals collected by the plurality of heart sound sensors comprised in the primary heart sound sensor and the secondary heart sound sensors; and
  determining a heart sound signal corresponding to the region to be monitored according to the signal average value.

18. The method of claim 17, wherein when a plurality of heart sound sensors are provided at different heart sound auscultation positions in the region to be monitored, the plurality of heart sound sensors is arranged in a preset arrangement mode, and the arrangement mode comprises:
 allowing the plurality of heart sound sensors to have an identical area of a vibration sensing region and to be arranged uniformly in an array; or
 allowing the plurality of heart sound sensors to comprise at least one sensor dense distribution region and a sensor sparse distribution region surrounding the sensor dense distribution region, an area of the vibration sensing region of the heart sound sensor located in the sensor dense distribution region being smaller than an area of the vibration sensing region of the heart sound sensor located in the sensor sparse distribution region, and a distribution density of the heart sound sensors located in the sensor dense distribution region being greater than a distribution density of the heart sound sensors located in the sensor sparse distribution region.

19. The method of claim 17, wherein the using the heart sound locator to determine a primary heart sound sensor and a secondary heart sound sensor in the plurality of heart sound sensors comprises:
 acquiring the vibration signals collected by the plurality of heart sound sensors within a first preset period of time;
 calculating heart sound envelopes corresponding to the vibration signals collected by the plurality of heart sound sensors at a plurality of time points within the first preset period of time;
 calculating heart sound components corresponding to the plurality of heart sound sensors and spectrum information about the heart sound components according to the heart sound envelopes corresponding to the plurality of heart sound sensors; and
 determining, in the spectrum information about the heart sound components corresponding to the plurality of heart sound sensors, at least one heart sound sensor corresponding to a heart sound component having a center frequency point whose difference from the preset center frequency point of the region to be monitored falls within a preset numerical range and having the highest spectral energy, as the primary heart sound sensor.

20. The method of claim 17, wherein the using the heart sound analyzer to monitor vibration signals of the primary heart sound sensor and the secondary heart sound sensor and determining the heart sound signal of the region to be monitored comprises:
 acquiring the vibration signals collected by the primary heart sound sensor and the secondary heart sound sensor within a second preset period of time;
 calculating a signal average value of the vibration signals collected by the plurality of heart sound sensors comprised in the primary heart sound sensor and the secondary heart sound sensor at a preset time point within the second preset period of time, a plurality of the preset time points being provided and each of the plurality of preset time points corresponding to one of the signal average value;
 calculating heart sound envelopes corresponding to the signal average value;
 calculating heart sound components corresponding to the signal average value and spectrum information about the heart sound components according to the heart sound envelopes corresponding to the signal average value; and
 comparing the spectrum information about the heart sound components with preset standard spectrum information corresponding to the region to be monitored, and acquire a heart sound signal corresponding to the region to be monitored.

\* \* \* \* \*